(12) United States Patent
Lavergne et al.

(10) Patent No.: US 8,173,721 B2
(45) Date of Patent: *May 8, 2012

(54) POLYMER CEMENT FOR PERCUTANEOUS VERTEBROPLASTY

(75) Inventors: Claudine Lavergne, Caixon (FR); Alain Leonard, Caixon (FR)

(73) Assignee: Teknimed, Vic-En-Bigorre (FR)

( * ) Notice: Subject to any disclaimer, the term of this patent is extended or adjusted under 35 U.S.C. 154(b) by 624 days.

This patent is subject to a terminal disclaimer.

(21) Appl. No.: 10/871,036

(22) Filed: Jun. 21, 2004

(65) Prior Publication Data

US 2005/0256220 A1 Nov. 17, 2005

(30) Foreign Application Priority Data

May 14, 2004 (FR) .................................. 04 05249

(51) Int. Cl.
*A61F 2/02* (2006.01)
(52) U.S. Cl. .................. 523/117; 523/115; 523/116
(58) Field of Classification Search .................. 523/117, 523/116
See application file for complete search history.

(56) References Cited

U.S. PATENT DOCUMENTS

| | | | | |
|---|---|---|---|---|
| 4,500,658 | A * | 2/1985 | Fox | 523/117 |
| 5,795,922 | A * | 8/1998 | Demian et al. | 523/117 |
| 5,902,839 | A * | 5/1999 | Lautenschlager et al. | 523/115 |
| 5,914,356 | A * | 6/1999 | Erbe | 523/114 |
| 6,309,420 | B1 * | 10/2001 | Preissman | 623/16.11 |
| 7,008,433 | B2 * | 3/2006 | Voellmicke et al. | 606/93 |
| 2003/0031698 | A1 * | 2/2003 | Roeder et al. | 424/423 |
| 2005/0255159 | A1 * | 11/2005 | Hyers et al. | 424/484 |

FOREIGN PATENT DOCUMENTS

| | | | |
|---|---|---|---|
| CA | 2158402 | * | 3/1996 |
| EP | 1595553 A1 | | 11/2005 |
| EP | 1595553 B1 | | 4/2007 |

OTHER PUBLICATIONS

JASPER, L. E. et al.: "Material properties of various cements for use with vertebroplasty", Journal of Materials Science: Materials in Medicine, vol. 13, No. 1, Jan. 2002, pp. 1-5, XP-002312782.
Garcia Carrodeguas, R. et al.: "Injectable Acrylic Bone Cements for Vertebroplasty with Improved Properties", Journal of Biomedical Materials Research, vol. 68, No. 1, Jan. 15, 2004, pp. 94-104, XP-002312783.
Mathis, J. M. et al.: "Percutaneous Vertebroplasty: A Developing Standard of Care for Vertebral Fractures", American Journal of Neuroradiology, vol. 22, Feb. 2001, pp. 373-381, XP-002312784.
Wallaeys R. (1952), Ann. Chim., 7:808-848.
Osaka et al. (1991), J. Master. Sci. Mat. Med., 2:51-55.
European Search Report, Application No. EP05352009.4, Mail Date: Sep. 23, 2005.
Decision to Grant European Patent, Application No. EP05352009.4, Mail Date: Mar. 29, 2007.

* cited by examiner

*Primary Examiner* — Tae H Yoon
(74) *Attorney, Agent, or Firm* — Brian P. Hopkins, Esq.; Muriel Liberto, Esq.

(57) ABSTRACT

A fluid cement for medical use for bone reconstruction, in particular for filling the vertebral body, and a binary composition which is intended for the preparation of such a cement. A device for conditioning the binary composition, and a method of preparing a bone cement from a binary composition. The fluid cement according to the invention comprises: a) approximately 70% to 85% by weight of a polymer comprising a polymethylmethacrylate and a methylmethacrylate monomer, and b) approximately from 15 to 30% by weight of a radio-opaque composition. Preferably, the radio-opaque composition comprises a radio-opacifier, such as a barium sulphate and zirconium dioxide, in a mixture with a calcium phosphate, for example hydroxyapatite.

11 Claims, No Drawings

POLYMER CEMENT FOR PERCUTANEOUS VERTEBROPLASTY

The present invention relates to the field of polymeric cements, in particular acrylic cements, used for repairing bone and joint traumas.

The subject thereof is a fluid cement for medical use in bone reconstruction, in particular for filling the vertebral body, and also a binary composition intended for the preparation of such a cement. Another subject of the present invention is a conditioning device for said binary composition. A method of preparing bone cement from a binary composition is likewise claimed.

Bone cements have been used for a number of years in order to assist the attachment of artificial implants to the skeleton. The cement which serves as a junction between the bone and the implant must meet a certain number of requirements, in particular mechanical, but must also be non-toxic and biocompatible. Certain cements have even been studied for their bioactive properties, i.e. for their action which assists the adhesion and the cellular growth on the implant.

Since the middle of the eighties, the use of cements has widened to bone repair, and primarily to percutaneous vertebroplasty. This minimally invasive technique allows injection of a cement through a trocar into a fractured vertebra in order to ensure bone volume and stabilisation. The first percutaneous vertebroplasty was achieved in 1984 and has since enjoyed increasing success, opening the way to plastic repair of other types of bone.

The cements which have been used to date are organic polymers, formed from a mixture of a prepolymer, generally PMMA (methyl polymethylmethacrylate) and from a monomer, generally MMA (methyl methylmethacrylate), reacting in the presence of a polymerisation activator. For use in vivo, which does not allow high temperatures, a reaction initiator is added.

Most commercially available cements are available in the form of two separate components: a powder comprising principally prepolymer balls and a liquid containing principally the monomer. The initiator, for example benzoyl peroxide (BPO), is generally incorporated with the powder, while the liquid contains a chemical activator (catalyst), such as dimethylparatoluidine (DMPT), the polymerisation reaction starting when the two components are mixed. In order to avoid spontaneous polymerisation which can possibly occur during storage, there is incorporated furthermore in the liquid component a stabiliser, commonly hydroquinone. The activator and the initiator are introduced in the proportion of 1 to 2% in the corresponding component, the stabiliser itself taking effect at some tens of ppm.

In order to display the cement visually during and after the operation by radiological means, a radio-opaque substance can be added, most often barium sulphate ($BaSO_4$) or zirconium dioxide ($ZrO_2$). Commercial cements contain a quantity thereof of the order of 10% in the powder.

These binary compositions for the preparation of bone cements, designed originally for attachment of implants and sealing of prostheses, fulfil the criteria of resistance to traction and to compression, of chemical neutrality and of biocompatibility. They are authorised for medical use and have proved their qualities in the long term when the skeleton is subjected to large, repeated forces. This is why bone cements for attaching implants have been adopted as the preferred material for bone reconstruction surgery.

However, the conditions for using cements in percutaneous surgery imply that a certain number of specific requirements must be respected, at the risk of accidents, the effects of which can be dramatic for the patient, such as paraplegia. This is why the practitioner must use a cement which is sufficiently fluid for it to flow through a trocar with a diameter of a few millimetres, and for it to maintain this fluidity long enough for the practitioner to have the time to operate at leisure. In so doing, the physical characteristics of the cement after polymerisation must be preserved.

On the other hand, the cement injected even in small quantities must be visually displayed permanently during the operation which is not the case with the currently marketed compositions. Although certain ones contain a radio-opacifier, correct visual display during percutaneous injection is not obtained. This leads the practitioners to modify the compositions themselves, with the risk of modifying at the same time the physical characteristics of the cement, in particular its viscosity and its rate of hardening, and its resistance properties after polymerisation.

Hence, the currently known cements, even if they are efficient in attaching implants to the skeleton, have not been designed for a treatment stabilising the vertebral body by a percutaneous route and do not take into account the specificities connected to this technique.

The object of the present invention is to provide a material suitable for percutaneous surgical use, in particular for filling the vertebral body, said material having a suitable intra-operative and post-operative behaviour i.e.:
fluidity,
setting time greater than 15 minutes,
opacity during fluoroscopy,
resistance to compression: at least 70 Mpa,
resistance to bending: at least 50 Mpa,
flexural modulus: at least 1,800 Mpa.

Of course, such a cement must be compatible with medical use from the point of view of its toxicity and its biocompatibility.

Unexpectedly, it was found that it was possible to formulate a cement based on polymethylmethacrylate and methylmethacrylate monomer fulfilling the specifications above, by incorporating in said cement high quantities of a radio-opaque composition, without the qualities demanded for intended use being altered.

More precisely, the subject of the present invention is a fluid cement for medical use for filling the vertebral body, comprising:
a) approximately 70% to 85% by weight of a polymer comprising a polymethylmethacrylate and a methylmethacrylate monomer, and
b) approximately from 15% to 30% by weight of a radio-opaque composition.

Preferably, the cement according to the invention comprises:
a) at least approximately 70% by weight of a polymer comprising a polymethylmethacrylate and a methylmethacrylate monomer, and
b) at least approximately 25% by weight of a radio-opaque composition.

The cement according to the invention has good fluidity in the minutes following the bringing together of the ingredients, the component, and can be worked up to 10 minutes and more after its preparation. The polymerisation reaction causes the mass setting of the polymethylmethacrylate and of the monomer which disappear in order to form a solid polymer cement. In the present application, the term "cement" or "fluid cement" corresponds to the cement as occurs after mixing the ingredients. The composition of the cement will be considered as that of the fluid cement which is ready for use, before solidification.

Polymethylmethacrylate (or PMMA) and methylmethacrylate monomer (or MMA) which go into the composition of the cement according to the invention, are those commonly used for the preparation of acrylic cements. The PMMA powders occur in the form of polymer balls. The molar mass of these powders is between 150,000 and 1,500,000 g/mol. The average diameter of the particles is between 30 µm and 100 µm. The monomer is the methylic ester of methacrylic acid. MMA and PMMA for medical use are commercially available.

The radio-opaque composition represents a large fraction of the cement. It has the aim of allowing injection of the cement under continuous control by fluoroscopy, in particular during vertebroplasty procedures. It can be formed by a pure radio-opaque compound or as a mixture with other ingredients. It has been found that the combination of a calcium phosphate and a radio-opaque compound allowed a cement to be obtained which was readily visible during its positioning and subsequently well tolerated by the organism. Advantageously, the radio-opaque composition present in the cement according to the invention comprises a radio-opaque compound and calcium phosphate.

The recommended usage proportions of the radio-opaque compound and of the calcium phosphate, by weight relative to the total weight of the cement, are such that said radio-opaque composition comprises approximately 20% to 27% of a radio-opaque compound and approximately 3% to 6% of calcium phosphate. Preferably, the radio-opaque composition comprises approximately 27% of a radio-opaque compound and approximately 3% of calcium phosphate.

The radio-opaque compound can be chosen from compounds which are known and compatible with medical use. Said compound is preferably chosen within the group composed of barium sulphate and zirconium dioxide. Barium sulphate ($BaSO_4$) is a radio-opacifier commonly used in cements for implant attachment, the innocuousness of which is recognised. It occurs in general in the form of powder, the particles of which have an average diameter of 1 to 10 µm. Zirconium dioxide ($ZrO_2$) can be used alternatively. It is introduced in the form of powder, the particles of which have an average diameter of 20 µm.

The radio-opaque composition can comprise a mixture with the radio-opacifier, calcium phosphate. Advantageously, the calcium phosphate is apatite hydroxide. Advantageously, there can be used a phosphocalcic hydroxyapatite of the formula $Ca_{10}(PO_4)_6(OH)_2$, with a Ca/P ratio of 1.667 and a granulometry less than 30 µm. The introduction of this ingredient into the composition brings a doubly beneficial effect, on the one hand by improving the homogeneity of the cement and consequently its malleability, and on the other hand by increasing its biocompatibility. In fact, it is known that hydroxyapatite assists the bone regrowth by stimulating the biological activity of the osteoblasts and their proliferation. It has been studied for this reason without its mechanical properties being otherwise turned to good account.

The introduction into the cement of a large quantity of opacifying composition has repercussions on its physical and chemical characteristics, in particular its fluidity, its solidification rate and its mechanical resistance. In order to obtain optimal functional properties it is recommended to keep to the proportions of ingredients as defined by the present application, and which are likewise the subject of the present invention.

In particular, in the cement according to the invention, polymethylmethacrylate and methylmethacrylate monomer are advantageously provided in a weight ratio between 1 and 2. Preferably, the ratio PMMA/MMA is between 1.4 and 1.5.

Hence, surprisingly, it has been determined that the optimal formulation is the one where the proportion of PMMA is less than in standard formulations, the addition of the opacifying composition being essentially to the detriment of the polymethylmethacrylate.

The cement according to the invention can finally contain a certain number of reagents assisting the control of the polymerisation. In particular, it can comprise, in addition to the ingredients mentioned above, an effective quantity of one or more of the following reagents: a chemical polymerisation activator, a polymerisation initiator, a stabiliser. The person skilled in the art knows these reagents and has mastered their use.

A reaction initiator can advantageously be chosen among the polymerisation catalysts, such as benzoyl peroxide (BPO). The activator or accelerator of the polymerisation reaction is preferably N,N-dimethylparatoluidine (DMPT). The stabiliser, preferably hydroquinone, can be added in order to avoid premature polymerisation of the monomer as a result of exposure to heat or light. These reagents are effective in very small concentrations which the person skilled in the art can adjust as a function of the desired kinetics. They go into the composition of the cement in quantities of the order of 0.2% to 2% for benzoyl peroxide, of 1.5% to 2.5% for DMPT, and approximately 20 ppm as far as hydroquinone is concerned. According to a preferred formulation, there is used 0.4% to 0.6% of benzoyl peroxide; 2.4% of DMPT and 20 ppm of hydroquinone.

The cement according to the invention, once ready, will react in order to form a solid mass in a relatively short period of time (a few minutes to a few tens of minutes), the formulation claimed here setting at the earliest in 15 minutes. It is evident that the ingredients reacting together must be mixed solely at the moment of use. This is why it is convenient to use two pre-mixtures of ingredients which it suffices to bring together in order to prepare the cement according to the invention. These pre-mixtures, one in powder form, the other in liquid form, form the two components of a binary composition which is intended for the preparation of a bone cement according to the invention.

According to the invention, said binary composition is composed of a liquid component L comprising a methylmethacrylate monomer and a powder component P comprising a polymethylmethacrylate, in which the powder component P comprises approximately 25 to 50% by weight relative to the weight of powder of a radio-opaque composition.

Advantageously, in the binary composition according to the invention, the powder component P comprises at least approximately 35%, preferably at least approximately 45% by weight relative to the weight of powder of a radio-opaque composition.

According to an interesting feature of the invention, said radio-opaque composition comprises a radio-opaque compound and calcium phosphate. Advantageously, the radio-opaque composition comprises approximately 30% to 45% of a radio-opaque compound and approximately 5% to 10% of calcium phosphate, by weight relative to the weight of powder. According to a preferred formulation, the radio-opaque composition comprises approximately 45% of a radio-opaque compound and approximately 5% of calcium phosphate, by weight relative to the weight of powder.

Said radio-opaque compound can be chosen within the group composed of barium sulphate and zirconium dioxide. As far as calcium phosphate is concerned, apatite hydroxide is chosen preferably.

The binary composition according to the invention comprises in addition preferably an effective quantity of one of more of the following reagents:

- in the liquid component L, a chemical polymerisation activator;
- in the powder component P, a polymerisation initiator and a stabiliser.

For example, the liquid component L can comprise from 1.5% to 2.5% of DMPT. The powder component P can comprise from 0.2% to 2% of benzoyl peroxide and 20 ppm of hydroquinone. Preferably, the liquid component L contains 2.4% of DMPT, whilst the powder component P contains 0.5±0.1% of PBO.

During use in the operating theatre, the two components, powder and liquid, are mixed. At this moment, the powder phase dissolves into the liquid phase, thus giving a mixture which must be sufficiently fluid to be able to be injected into a vertebral body. In the course of the mixing, the activator and the initiator react in order to produce free radicals. These radicals initiate the polymerisation reaction which leads to progressive hardening of the cement, according to the desired kinetics. For good control of these criteria, the binary composition according to the invention is advantageously formulated such that the powder component P and the liquid component L are in a weight ratio P/L between 1 and 2, preferably between 1.4 and 1.5.

For practitioners, it is imperative to limit manipulations which are lengthy and a source of errors to the moment of operating. This is why it is convenient to use pre-mixtures of ingredients in separate receptacles. Another subject of the present invention is therefore a device which is intended for the preparation of a fluid cement for medical use according to the invention comprising:

i) a first receptacle containing a liquid component comprising at least one monomer of methylmethacrylate and possibly an effective quantity of a chemical polymerisation activator, preferably dimethylparatoluidine;

ii) a second receptacle containing a powder component comprising at least one polymethylmethacrylate and a radio-opaque composition, as described above, and possibly an effective quantity of a polymerisation initiator, preferably benzoyl peroxide and a stabiliser, preferably hydroquinone.

In other words, a device is claimed which is intended for the preparation of a fluid cement for medical use from a binary composition according to the invention, comprising:

i) a first receptacle containing the liquid component L, and
ii) a second receptacle containing the powder component P.

The device according to the invention can be used advantageously for the preparation of a fluid cement for medical use for filling the vertebral body.

Another subject of the present invention is a method of preparing a fluid cement for medical use for filling the vertebral body, comprising essentially the step consisting in mixing into a homogeneous mass a powder component P and a liquid component L, as are described above. According to an advantageous variant of the claimed method, the powder component P and the liquid component L are introduced in a weight ratio P/L between 1 and 2. Preferably, the components P and L are provided in a weight ratio P/L between 1.4 and 1.5.

The method according to the invention can be implemented advantageously for the preparation of a fluid cement for medical use for filling the vertebral body.

The following examples will allow better comprehension of the invention without in any way limiting the scope thereof. The following abbreviations are used:

PMMA: polymethylmethacrylate
MMA: methyl methacrylate
BPO: benzoyl peroxide
$BaSO_4$: barium sulphate
$ZrO_2$: zirconium dioxide
HAP: phosphocalcic hydroxyapatite
DMTP: dimethylparatoluidine
HQ: hydroquinone
P/L: ratio of powder phase/liquid phase, by weight.

EXAMPLE 1

Binary Composition 1

| POWDER PHASE (% by weight) | |
|---|---|
| PMMA: | 64.41 |
| BPO: | 0.59 |
| $BaSO_4$: | 25.00 |
| HAP | 10.00 |
| LIQUID PHASE (% by weight) | |
| MMA: | 97.60 |
| DMPT: | 2.40 |
| HQ: | 0.002 | with P/L = 1.41

EXAMPLE 2

Binary Composition 2

| POWDER PHASE (% by weight) | |
|---|---|
| PMMA: | 59.33 |
| BPO: | 0.54 |
| $ZrO_2$: | 30.08 |
| HAP: | 10.05 |
| LIQUID PHASE (% by weight) | |
| MMA: | 97.60 |
| DMPT: | 2.40 |
| HQ: | 0.002 | with P/L = 1.57

EXAMPLE 3

Binary Composition 3

| POWDER PHASE (% by weight) | |
|---|---|
| PMMA: | 49.43 |
| BPO: | 0.45 |
| $ZrO_2$: | 40.01 |
| HAP: | 10.11 |

-continued

| LIQUID PHASE (% by weight) | |
|---|---|
| MMA: | 97.60 |
| DMPT: | 2.40 |
| HQ: | 0.002 | with P/L = 1.47

EXAMPLE 4

Binary Composition 4

| POWDER PHASE (% by weight) | |
|---|---|
| PMMA: | 49.50 |
| BPO: | 0.45 |
| $ZrO_2$: | 45.06 |
| HAP: | 4.99 |
| LIQUID PHASE (% by weight) | |
| MMA: | 97.60 |
| DMPT: | 2.40 |
| HQ: | 0.002 | with P/L = 1.48

EXAMPLE 5

Method of Preparing a Bone Cement

Powder Component:

The powder phase is obtained by screening the various ingredients at 200 μm, then mixing by agitation for one minute, for example in a multiflux mixer.

Liquid Component:

The liquid phase is prepared by dissolving hydroquinone in the monomer MMA. The agitation is maintained until complete dissolution. DMPT is then added.

The two phases are conditioned separately in receptacles suitable for their preservation. The instantaneous preparation kits comprise a receptacle containing the liquid phase and a receptacle containing the powder phase.

Binary Composition

During use in the operating theatre, the receptacles are opened and their content is mixed. The powder dissolves rapidly into the liquid phase giving a fluid mixture which is injected into the vertebral body of the patient through an adequate tube. The initiator BPO and the activator DMPT react to form free radicals which initiate the progressive polymerisation reaction of the cement. The surgeon then has about fifteen minutes to operate, controlling the procedure permanently by fluoroscopy.

EXAMPLE 6

Preparation of Hydroxyapatite

The hydroxyapatite which is used is obtained by precipitation in an aqueous medium. This method is based on neutralisation of orthophosphoric acid by calcium hydroxide, as described by Wallaeys (Wallaeys R., 1952, "Contribution à l'étude des apatite phosphocalciques", Ann. Chim., 7, pp. 808-848) and repeated by Osaka (Osaka A., Miura Y., Takeuchi K., Asada M. and Takahashi K., 1991, "Calcium apatite prepared from calcium hydroxide and orthophosphoric acid", J. Mater. Sci. Mat. Med., 2, pp. 51-55). The reaction which is initiated is the following:

$$6H_3PO_4 + 10\ Ca(OH)_2 \rightarrow Ca_{10}(PO_4)_6(OH)_2$$

This little used method has the huge advantage of being non-polluting because the reaction medium is demineralised water. The reaction does not generate any toxic component which risks impairing the biocompatibility of the bone cement.

The method of fabrication takes place in the following manner:

After calcination at 900° C., the calcium hydroxide is suspended in demineralised water, to which a solution of diluted phosphoric acid is added. After maturation, the reaction product is filtered, dried in an oven, then ground and screened with various screens. Then the thus obtained powder is calcinated at a temperature between 900° C. and 1100° C. A final screening allows the fraction of a granulometry less than 30 μm to be recovered.

EXAMPLE 7

ISO Standard Tests

Standard ISO 5833, entitled, "Surgical implants, implants based on acrylic resin" defines the characteristics required by regulations and the standard tests allowing these characteristics to be quantified. The compositions described in examples 1 to 4 above were tested.

A first series of tests relates to the properties of the cement during use, i.e. the setting time, the maximum temperature achieved by the cement during polymerisation, and the kneading time. The results obtained for the four compositions are presented in Table 1.

A second series of tests relates to the properties of the installed cement, i.e. the resistance to compression, the resistance to bending and the flexural modulus. The results obtained with the compositions 1, 3 and 4 are presented in Table 2.

All the operating modes are described in detail in the standard ISO 5833.

TABLE 1

| | setting time (mn) | max. temperature (° C.) | kneading time (mn) |
|---|---|---|---|
| Composition 1 | 17.80 | 73.9 | 10.75 |
| Composition 2 | 15.66 | 73.3 | 10.20 |
| Composition 3 | 18.46 | 67.9 | 9.50 |
| Composition 4 | 18.05 | 69.5 | 9.00 |

TABLE 2

| | resistance to compression (Mpa) | resistance to bending (Mpa) | flexural modulus (Mpa) |
|---|---|---|---|
| Composition 1 | 84.2 | 58.2 | 3345 |
| Composition 3 | 88.4 | 58.1 | 4043 |
| Composition 4 | 74.6 | 57.6 | 3461 |

The obtained results show that the cements according to the invention are in accordance with regulations in strength and can be used as surgical implants.

It is noted likewise that their characteristics fulfil the specifications defined above for cements which can be used in percutaneous vertebroplasty (setting time greater than 15 minutes), opacity during fluoroscopy, with the retention of the characteristics of resistance to compression, resistance to bending and flexural modulus.

The invention claimed is:

1. A binary composition comprising a liquid component L and a powder component P,
    wherein the liquid component comprises a methylmethacrylate monomer, a polymerization activator, and stabilizer;
    wherein the powder component comprises a polymethylmethacrylate homopolymer, a polymerization initiator and at least 35% of a radio-opaque composition, wherein the radio-opaque composition comprises 30-45% of a radio-opaque compound and 5-10% calcium phosphate, and
    wherein the powder component P and the liquid component L are provided in a weight ratio P/L between 1.4 and 1.5.

2. A binary composition according to claim 1, wherein said radio-opaque compound is barium sulphate or zirconium dioxide.

3. A binary composition according to claim 1, wherein the calcium phosphate is hydroxyapatite.

4. A device intended for preparation of a fluid cement for medical use from a binary composition according to claim 1, comprising:
    i) a first receptacle containing the liquid component L, and
    ii) a second receptacle containing the powder component P.

5. A method of preparing a fluid cement, for medical use, for filling the vertebral body, comprising essentially the step consisting in mixing the components made of powder P and liquid L according to claim 1 into a homogeneous mass in a weight ratio P/L between 1.4 and 1.5.

6. A binary composition according to claim 1, wherein the chemical polymerisation activator is dimethylparatoluidine.

7. A binary composition according to claim 1, wherein the polymerisation initiator is benzoyl peroxide and the stabiliser is hydroquinone.

8. A fluid cement, for medical use, for filling the vertebral body, comprising:
    a) approximately 80% by weight of a polymer comprising a polymethylmethacrylate homopolymer, methylmethacrylate monomer, a polymerization activator, initiator, and stabilizer; and
    b) approximately 20% by weight of a radio-opaque composition, wherein the radio-opaque composition comprises a radio-opaque compound and hydroxyapatite, wherein the radio-opaque compound makes up approximately 14% by weight of the fluid cement, and wherein the calcium phosphate makes up approximately 6% by weight of the fluid cement.

9. A fluid cement, for medical use, for filling the vertebral body, comprising:
    a) approximately 76% by weight of a polymer comprising a polymethyimethacrylate homopolymer, methylmethacrylate monomer, a polymerization activator, initiator, and stabilizer; and
    b) approximately 24% by weight of a radio-opaque composition, wherein the radio-opaque composition comprises a radio-opaque compound and hydroxyapatite, wherein the radio-opaque compound makes up approximately 18% by weight of the fluid cement, and wherein the calcium phosphate makes up approximately 6% by weight of the fluid cement.

10. A fluid cement, for medical use, for filling the vertebral body, comprising:
    a) approximately 70% by weight of a polymer comprising a polymethylmethacrylate homopolymer, methylmethacrylate monomer, a polymerization activator, initiator, and stabilizer; and
    b) approximately 30% by weight of a radio-opaque composition, wherein the radio-opaque composition comprises a radio-opaque compound and hydroxyapatite, wherein the radio-opaque compound makes up approximately 24% by weight of the fluid cement, and wherein the hydroxyapatite makes up approximately 6% by weight of the fluid cement.

11. A fluid cement, for medical use, for filling the vertebral body, comprising:
    a) approximately 70% by weight of a polymer comprising a polymethylmethaerylate homopolymer, methylmethacrylate monomer, a polymerization activator, initiator, and stabilizer; and
    b) approximately 30% by weight of a radio-opaque composition, wherein the radio-opaque composition comprises a radio-opaque compound and hydroxyapatite, wherein the radio-opaque compound makes up approximately 27% by weight of the fluid cement, and wherein the hydroxyapatite makes up approximately 3% by weight of the fluid cement.

* * * * *